US008697926B2

(12) United States Patent
Menéndez Sastre et al.

(10) Patent No.: US 8,697,926 B2
(45) Date of Patent: Apr. 15, 2014

(54) METHOD FOR OBTAINING AROMATIC HYDROCARBONS FROM METHANE

(75) Inventors: Miguel Menéndez Sastre, Zaragoza (ES); Javier Herguido Huerta, Zaragoza (ES); Carlos Téllez Ariso, Zaragoza (ES); Jaime Soler Herrero, Zaragoza (ES); María Pilar Gimeno Tolosa, Zaragoza (ES)

(73) Assignee: Universidad de Zaragoza, Zaragoza (ES)

( * ) Notice: Subject to any disclaimer, the term of this patent is extended or adjusted under 35 U.S.C. 154(b) by 374 days.

(21) Appl. No.: 13/000,230

(22) PCT Filed: Jun. 19, 2009

(86) PCT No.: PCT/ES2009/070240
§ 371 (c)(1),
(2), (4) Date: Mar. 15, 2011

(87) PCT Pub. No.: WO2009/153381
PCT Pub. Date: Dec. 23, 2009

(65) Prior Publication Data
US 2011/0160507 A1 Jun. 30, 2011

(30) Foreign Application Priority Data
Jun. 20, 2008 (ES) ................... 200801857

(51) Int. Cl.
*C07C 15/00* (2006.01)
(52) U.S. Cl.
USPC ............ 585/407; 585/412; 585/415; 585/417

(58) Field of Classification Search
USPC ......... 585/407, 412, 415, 417, 418, 420, 421, 585/943
See application file for complete search history.

(56) References Cited

U.S. PATENT DOCUMENTS

| 4,120,910 A | 10/1978 | Chu |
| 5,026,937 A * | 6/1991 | Bricker ........................ 585/415 |
| 2005/0143610 A1 | 6/2005 | Mitchell |
| 2006/0013762 A1 | 1/2006 | Kuipers |

(Continued)

FOREIGN PATENT DOCUMENTS

| CN | 101244969 | 8/2008 |
| EP | 0228267 | 7/1987 |

(Continued)

OTHER PUBLICATIONS

Tsotsis et al. Catalytic Membrane Reactors. Computer-Aided Desing of Catalysts. 1993. pp. 471-474 http://books.google.com/books?id=IWGmX7EP5XkC&source=gbs_navlinks_s.*

(Continued)

*Primary Examiner* — Walter D Griffin
*Assistant Examiner* — Jelitza Perez
(74) *Attorney, Agent, or Firm* — Merchant & Gould P.C.

(57) ABSTRACT

Process for obtaining aromatic hydrocarbons from a stream containing at least one light hydrocarbon selected from the list comprising methane, ethane, ethylene, propane, propene, propylene, butane, butene or butadiene, which comprises putting said stream into contact with a catalyst, which comprises a catalytic material and a binder, in a fluidized bed reactor. Said reactor may have two reaction zones, an oxidizing zone and a reducing zone.

12 Claims, 5 Drawing Sheets

(56) References Cited

U.S. PATENT DOCUMENTS

| | | |
|---|---|---|
| 2007/0129587 A1 | 6/2007 | Iaccino |
| 2007/0249880 A1* | 10/2007 | Iaccino et al. ............... 585/418 |
| 2007/0276171 A9 | 11/2007 | Iaccino |
| 2007/0293709 A1* | 12/2007 | Iaccino et al. ............... 585/312 |

FOREIGN PATENT DOCUMENTS

| | | |
|---|---|---|
| WO | WO 0104237 | 1/2001 |
| WO | WO 0210099 | 7/2002 |
| WO | WO 03000826 | 1/2003 |
| WO | WO 2006068800 | 6/2006 |
| WO | WO 2007123523 | 11/2007 |
| WO | WO 2007123977 | 11/2007 |

OTHER PUBLICATIONS

Werther, J. Fluidized Bed Reactors. Ullman's Encyclopedia of Industrial Chemistry. 2007. pp. 27-29.*

Wang et al., Catalysis Letters, 21, 35-41, 1993.

International Search Report of PCT/ES2009/070240 mailed Nov. 10, 2009 (English & Spanish).

Written Opinion of PCT/ES2009/070240 mailed Nov. 10, 2009 (English & Spanish).

International Preliminary Examination Report of PCT/ES2009/070240 issued Feb. 8, 2011 (English & Spanish).

Mallada et al., Inorganic Membranes, Synthesis, Characterization and Applications, Membrane Science and Technology Series, 13, Chapter 8, pp. 255-323 and Chapter 10, pp. 401-458, 2008.

Cook et al., "Conversion of methane to aromatics over Mo2C/ZSM-5 catalyst in different reactor types," *Applied Catalysis A: General*, vol. 365, Elsevier, 2009, pp. 34-41.

Gimeno et al., "Counteracting Catalyst Deactivation in Methane Aromatization with a Two Zone Fluidized Bed Reactor," Ind. Eng. Chem. Res., vol. 49, American Chemical Society, 2010, pp. 996-1000.

* cited by examiner

METHOD FOR OBTAINING AROMATIC HYDROCARBONS FROM METHANE

This application is a National Stage Application of PCT/ES2009/070240, filed Jun. 19, 2009, which claims benefit of Serial No. P200801857, filed Jun. 20, 2008 in Spain and which applications are incorporated herein by reference. To the extent appropriate, a claim of priority is made to each of the above disclosed applications.

PRIOR ART

The energy crisis derives from the exhaustion of oil reserves, whose price increases and whose production may be insufficient to meet the demand. Meanwhile, there are large reserves of natural gas, but its transportation is very expensive, for which reason it is desirable to transform it into combustible liquids, which can be transported more easily. A channel which has awoken interest in recent years is the aromatization of methane, the main component of natural gas. In this reaction, methane is transformed into other hydrocarbons, such as ethane, ethylene, benzene, toluene, xylene and naphthalene, among others.

This aromatization reaction has been widely studied; many catalysts have been described for this. For example, patent application EP0228267 discloses a catalyst based on a group VIIB metal on a zeolite with gallium, while international patent application WO0210099 discloses a molybdenum catalyst supported on an aluminosilicate of type MFI. Among the most satisfactory, we have those based on molybdenum on an H-ZSM5 zeolite support (see L. Wang, et al., Catal. Lett. (1993), vol. 21, pp. 35).

Several processes have also been disclosed to carry out the reaction; thus international patent application WO2007/123977 discloses a process wherein two reactors are used with different temperature. International patent application WO2007/123523 discloses a process wherein the methane is put into contact with a catalyst to perform the aromatization reaction and a part of the catalyst is taken to a heating zone wherein it is heated, putting it into contact with hot combustion gases and the hot catalyst is returned to the reaction zone.

Another international patent application WO2006/068800 discloses a process wherein aromatic hydrocarbons are obtained from methane, which is put into contact with an alkylating agent to obtain alkylated aromatic hydrocarbons. A system has also been disclosed in international patent application WO03000826 wherein the methane is aromatized in a process wherein the catalyst, molybdenum on ZSM-5, and on a bed which could be a riser type fluidized bed, circulates from one reaction zone to a regeneration zone which are in different tanks.

A great variety of products are obtained in the aforementioned processes. In particular, the selectivity of methane to benzene is usually less than 80% and the yield does not exceed 6%-8%.

DESCRIPTION OF THE INVENTION

The present invention provides a catalyst for the aromatization process of methane, which is obtained by mixing a catalytic material, preferably consisting of a metal compound on a zeolite, with a binder, preferably clay, obtaining fluidizable particles, i.e. a catalyst is obtained with greater particle size.

Furthermore, the present invention provides an aromatization process of methane or of any other stream containing at least one light hydrocarbon, in a fluidized bed reactor, more preferably including two-zone fluidized bed reactors and by the use of a fluidizable catalyst as previously described, i.e. obtained by mixing a catalytic material and a binder.

We understand "catalytic material" in this description to be a catalyst known in the state of the art for these processes. This catalyst may contain a metal compound or a metal derivative and a support. The metal compound may be a metal or a metal oxide, carbide or nitride, such as, for example, but without being limiting in nature, molybdenum, cobalt, rhodium, iridium, nickel, palladium, calcium, magnesium, barium, lanthanum, scandium, cerium, titanium, zirconium, hafnium, vanadium, niobium, tantalum, chromium, tungsten, manganese, iron, ruthenium, cobalt, rhenium, indium, zinc, bismuth and transuranium metals. The support is an inorganic compound which may be, but without being limiting in nature, an oxide of aluminium, silica, titanium, this support may be amorphous or crystalline, and it is preferably a microporous or mesoporous material.

Examples of microporous crystalline materials include, but are not limited to, silicates, aluminosilicates, silicoaluminophosphates, alumina or any of their mixtures. More preferably, they are zeolites, which may be of any type ZSM-5, ZSM-8, ZSM-11, ZSM-23, ZSM-35, etc., even more preferably, they are of ZSM-5 type.

The mesoporous materials may preferably be of MCM type.

A binder is added to this "catalytic material" thus obtaining the catalyst of the present invention. The binder may be, but without being limited to, clay, silica, alumina or aluminophosphate, preferably it is clay. The resulting catalytic material after the binding process is characterized in that it has a greater particle size.

Therefore, an aspect of the present invention relates to a process for the aromatization of a stream containing at least one light hydrocarbon selected from the list comprising methane, ethane, ethylene, propane, propylene, butane, butene or butadiene and which consists of putting said stream into contact with a catalyst in a fluidized bed reactor, where said catalyst comprises a catalytic material and a binder.

This stream is preferably of methane and may include small quantities of ethane, ethylene or other light hydrocarbons, which is logical since these compounds are typically found together with methane in natural gas, and their presence improves the yield to aromatics. In addition to using methane from natural gas, this same process can be applied to methane obtained using other sources, for example methane obtained by fermentation, or to light petroleum gases.

The experimental studies described in the state of the art generally use a fixed bed reactor for this type of aromatization reactions, wherein the gas is fed from the upper part, and if it is fed from the lower part it is done at a velocity less than that of the minimum fluidization of the solid. In a fluidized bed reactor, such as that used in the present invention, the fluidization phenomenon consists of a gas being fed to the lower part of a particle bed, at sufficient velocity, greater than the minimum fluidization velocity, so that this particle bed starts behaving like a fluid. This phenomenon is known by any person skilled in the art.

Via the process of the present invention using a fluidized bed reactor, it has been observed that selectivity to benzene is much greater than that obtained with the same catalyst in a fixed bed reactor.

A preferred embodiment of the process of the present invention further comprises the use in the feed stream of an oxidizing or regenerating gas selected from the list comprising $H_2$, $O_2$, $CO_2$, $CO$, $H_2O$, $N_2O$ or any of their combinations, with or without inert gases. Preferably, the proportion of oxidizing or regenerating gases in the feed is up to 40% by weight of the total stream, and more preferably between 1% and 20%. In this way, it reduces the deactivation of the catalyst due to coke formation, when said gases react with the coke formed or with the catalyst and it produces the regeneration of the catalyst with $H_2$, $CO_2$, $H_2O$ or $O_2$, alone or mixed with inert gases, to eliminate the coke formed and restart the operation (i.e. operating continuously).

Another preferred embodiment of the process of the present invention comprises the use of the fluidized bed reactor as a two-zone reactor, an oxidizing zone and a reducing zone, characterized in that said reactor has a fluidized bed wherein a gasifying, oxidizing or regenerating agent is fed in the lower zone of the bed and the stream containing methane at an intermediate point of said bed.

In the two-zone reactor, a fluidized bed is used wherein an oxidizing or regenerating agent is fed in the lower zone of the bed and a hydrocarbon at an intermediate point. In this way, two zones are obtained: an oxidizing atmosphere is obtained in the lower zone and a reducing atmosphere in the upper zone. This makes it possible to perform a desired reaction with the hydrocarbon in the upper zone and regenerate the catalyst with the oxidizing or regenerating agent in the lower zone. The good mixture of the solid characteristic of the fluidized bed reactor facilitates the continuous transport of solid between the bed areas. In this case, the methane aromatization would be performed in the upper zone and the catalyst regeneration would be performed in the lower zone with a gasifying agent such as $H_2$, $H_2O$, $CO_2$ or $O_2$, alone or mixed with one another or with inert gases.

Another more preferred embodiment of the process of the invention comprises a fluidized bed reactor wherein the part of the reactor of the reducing zone has greater diameter than in the oxidizing zone.

The use of a different diameter in the lower zone and in the upper zone makes it possible to operate with very different flows in both areas, maintaining the fluidization conditions, which is advantageous in all those processes wherein the flow of the oxidizing agent in the lower zone is less than the flow of hydrocarbon which must be fed. Furthermore, it has the advantage of allowing a better linear velocity in the upper zone, which reduces the bubbling therein. Therefore, by decreasing the linear velocity in a fluidized bed and reducing the bubbling, the gas flow approximates the piston flow and the reactor efficiency is improved.

In other words, the advantage of having a different diameter in the lower zone and in the upper zone lies in the fact that there may be very different flows of the regenerator gas and of the methane stream, satisfying in both zones the need to maintain the gas velocity in the interval wherein the fluidization occurs whilst, if the diameter of the two zones is the same, the gas velocity would be more limited by that need.

Another preferred embodiment further comprises in the aforementioned two-zone reactors the use of inorganic membranes selective to hydrogen, inserted in the upper zone of the fluidized bed.

The hydrogen is removed from the reaction zone through said membranes, which makes it possible to obtain a greater conversion of methane or other light hydrocarbons, in accordance with Le Chatelier's principle. These membranes may be of any of the materials described in the field of inorganic membranes for the separation of hydrogen (see Inorganic membranes, synthesis, characterization and applications, R. Mallada and M. Menéndez, eds. Elsevier, 2008), such as Pd and its alloys or ceramic materials permeable to protons.

Throughout the description and the claims, the word "comprises" and its variants are not intended to exclude other technical characteristics, additives, components or steps. For persons skilled in the art, other objects, advantages and characteristics of the invention will be inferred in part from the description and in part from the practice of the invention. The following figures and examples are provided by way of illustration, and are not intended to limit the present invention.

EXAMPLES

Figure 1:
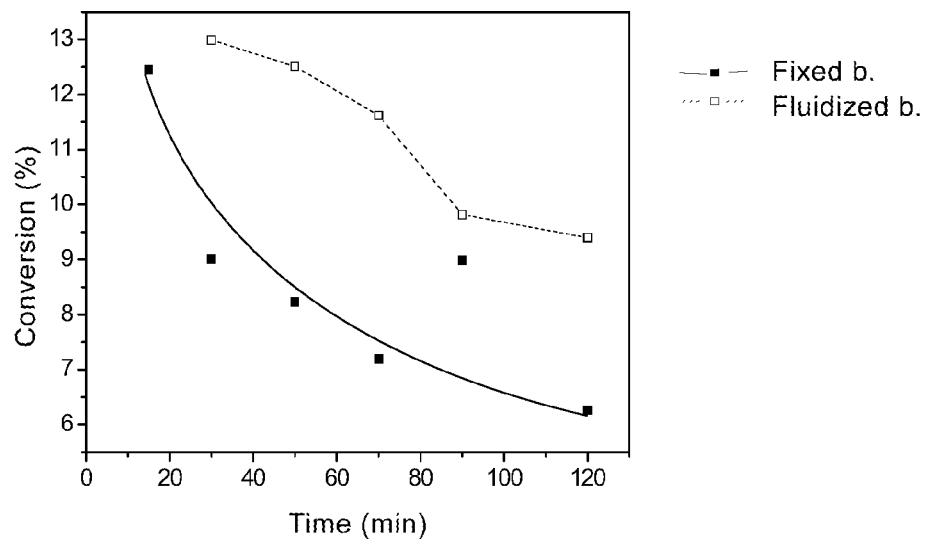
FIG. 1. Shows a graph of methane conversion in a fixed bed and in a fluidized bed.

Below, the invention will be illustrated by assays performed by the inventors, revealing the specificity and efficacy of the process of the invention.

Example 1

This example compares the results obtained in a fixed bed reactor and in a fluidized bed reactor. The conditions used therein should not be considered limiting of the scope of the invention.

The catalyst used was an HZSM5 zeolite (75% by weight) mixed with bentonite (25% by weight) whereto molybdenum was added until reaching 6% by weight of the total. The resulting solid was ground and screened to a particle size between 160 μm and 320 μm; 12 g of this catalyst were placed in a quartz reactor with an internal diameter of 3 cm with a porous quartz distribution plate, and 323 cm$^3$ (STP)/min of methane were fed, with 35.93 cm$^3$ (STP) of nitrogen to facilitate analysis of the products. The reaction was carried out during 2 hours in the fluidized bed reactor, obtaining the values of conversion (X), selectivity to hydrocarbons with 2 carbon atoms ($S_{C2}$), selectivity to benzene, total selectivity to aromatic hydrocarbons benzene+xylene+toluene ($S_{BTX}$) and yield to benzene ($Rto_B$) indicated in table 1. It can be verified that yields are obtained over 8%, described in other systems.

TABLE 1

Results of methane aromatization in fluidized bed

| Time (min) | X (%) | $S_{C2}$ (%) | $S_{Benzene}$ (%) | $S_{toluene}$ (%) | $S_{p\text{-}Xylene}$ (%) | $S_{o\text{-}Xylene}$ (%) | $S_{naphthalene}$ (%) | $S_{BTX}$ (%) | $R_{toB}$ (%) |
|---|---|---|---|---|---|---|---|---|---|
| 30 | 12.99 | 0.42 | 95.28 | 4.10 | 0.09 | 0.07 | 0.07 | 99.51 | 12.4 |
| 50 | 12.51 | 0.752 | 93.86 | 4.71 | 0.48 | 0.13 | 0.07 | 99.18 | 11.74 |
| 70 | 11.62 | 1.10 | 93.62 | 4.99 | 0.10 | 0.12 | 0.06 | 98.83 | 10.9 |

TABLE 1-continued

Results of methane aromatization in fluidized bed

| Time (min) | X (%) | $S_{C2}$ (%) | $S_{Benzene}$ (%) | $S_{toluene}$ (%) | $S_{p\text{-}Xylene}$ (%) | $S_{o\text{-}Xylene}$ (%) | $S_{naphthalene}$ (%) | $S_{BTX}$ (%) | $R_{toB}$ (%) |
|---|---|---|---|---|---|---|---|---|---|
| 90 | 9.81 | 1.21 | 93.48 | 4.97 | 0.14 | 0.14 | 0.06 | 98.73 | 9.2 |
| 120 | 9.40 | 1.68 | 92.89 | 5.08 | 0.10 | 0.17 | 0.07 | 98.25 | 8.7 |

The same experiment was performed in a fixed bed reactor with a similar feed flow to catalyst mass ratio (1500 cm³ (STP)/h. g catalyst), giving a much lower selectivity to benzene for similar conversion values, as is shown in the following table 2. In consequence, as is shown in this table, the yield to benzene is also less.

TABLE 2

Result of the methane aromatization in fixed bed

| Time (min) | X (%) | $S_{C2}$ (%) | $S_{Benzene}$ (%) | $S_{toluene}$ (%) | $S_{p\text{-}Xylene}$ (%) | $S_{o\text{-}Xylene}$ (%) | $S_{naphthalene}$ (%) | $S_{BTX}$ (%) | $R_{toB}$ (%) |
|---|---|---|---|---|---|---|---|---|---|
| 10 | 12.45 | 14.60 | 50.31 | 32.26 | 1.96 | 0.61 | 0.28 | 85.12 | 6.3 |
| 30 | 9.01 | 14.52 | 50.81 | 31.94 | 1.88 | 0.58 | 0.28 | 85.20 | 4.6 |
| 50 | 8.23 | 16.17 | 47.68 | 33.34 | 1.92 | 0.60 | 0.29 | 83.54 | 3.9 |
| 70 | 7.19 | 16.73 | 44.48 | 35.81 | 2.03 | 0.64 | 0.31 | 82.96 | 3.2 |
| 90 | 8.98 | 17.47 | 40.38 | 38.92 | 2.19 | 0.69 | 0.34 | 82.19 | 3.6 |
| 120 | 7.68 | 18.08 | 36.67 | 41.82 | 2.32 | 0.74 | 0.36 | 81.55 | 2.8 |

Figure 2:
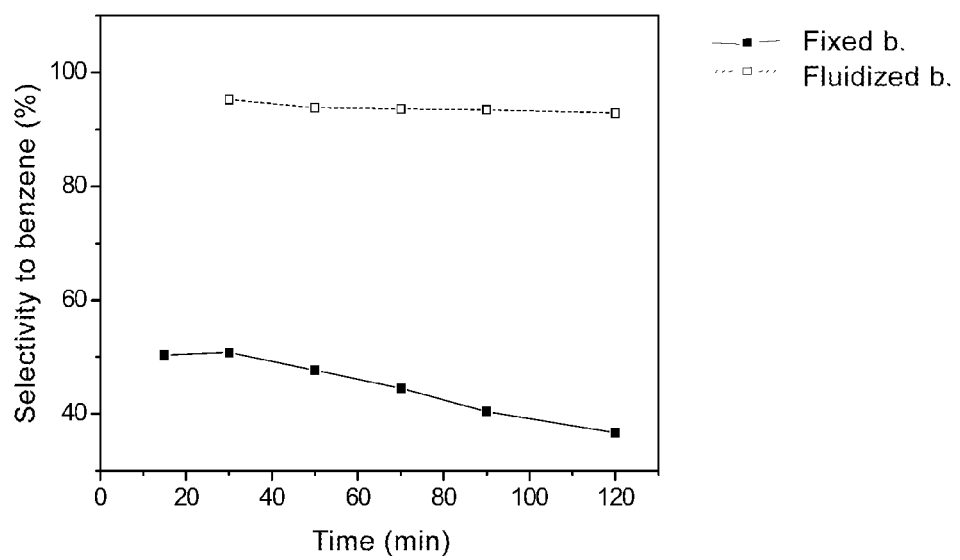
FIG. 2. Shows a graph of selectivity to benzene in a fixed bed and in a fluidized bed.

The comparison between the values obtained in the two reactors can be observed in the graphs of FIG. 1 and FIG. 2. The selectivities to benzene are greater than 90% using a fluidized bed reactor, while they are less than 50% using a fixed bed. The yield to benzene in the fluidized bed reactor is always greater than 8%.

Example 2

The following example describes the additional feed of an oxidizing agent in a two-zone fluidized bed reactor, achieving a better deactivation of the catalyst.

A catalyst was used from example 1 in a conventional fluidized bed reactor (cylindrical) and in a two-zone fluidized bed reactor, with trunk-conical shape (FIG. 3), feeding it in both cases with $CO_2$, as oxidizing agent, in the lower part.

Figure 3:
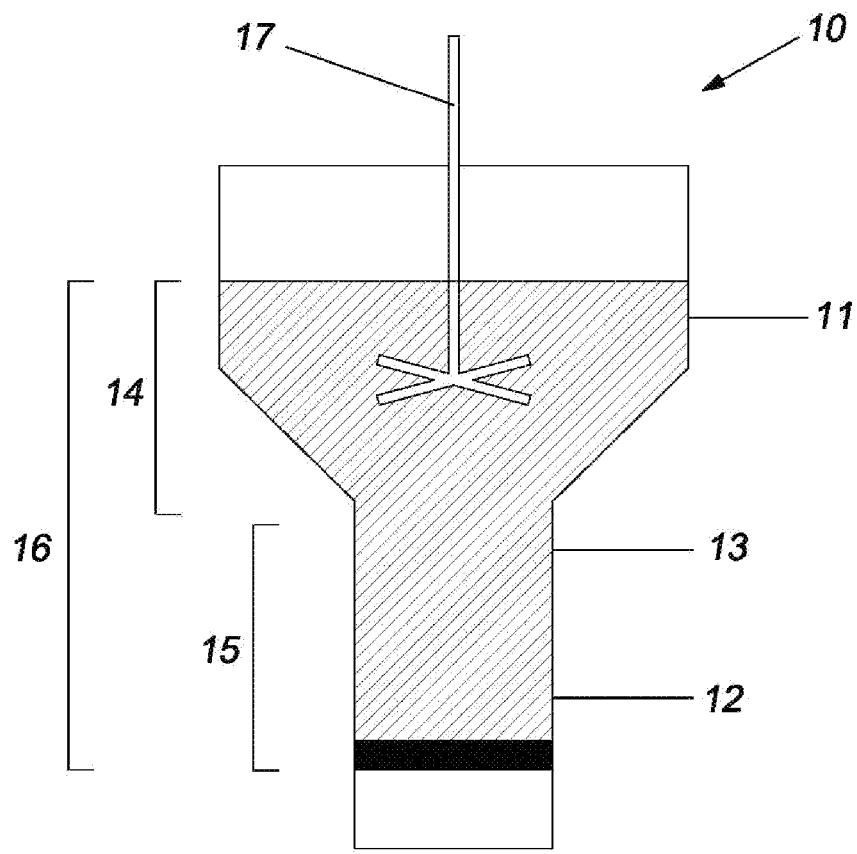
FIG. 3. Represents a two-zone fluidized bed reactor with different diameter in the lower zone and in the upper zone.

FIG. 3 shows a two-zone (11, 12) fluidized bed reactor (10) wherein the upper zone (11) has a greater section than the lower zone (12). A feed occurs with the oxidizing agent in the lower zone (12) of the bed (16), which produces an oxidizing atmosphere (15) in said lower zone (12) of the bed (16). Furthermore, a feed of the methane occurs, via a suitable distribution system of this gas stream (17), in an intermediate part (13) of the bed (16), which produces a reducing atmosphere (14) in the upper zone (11) of the bed (16).

Figure 4:
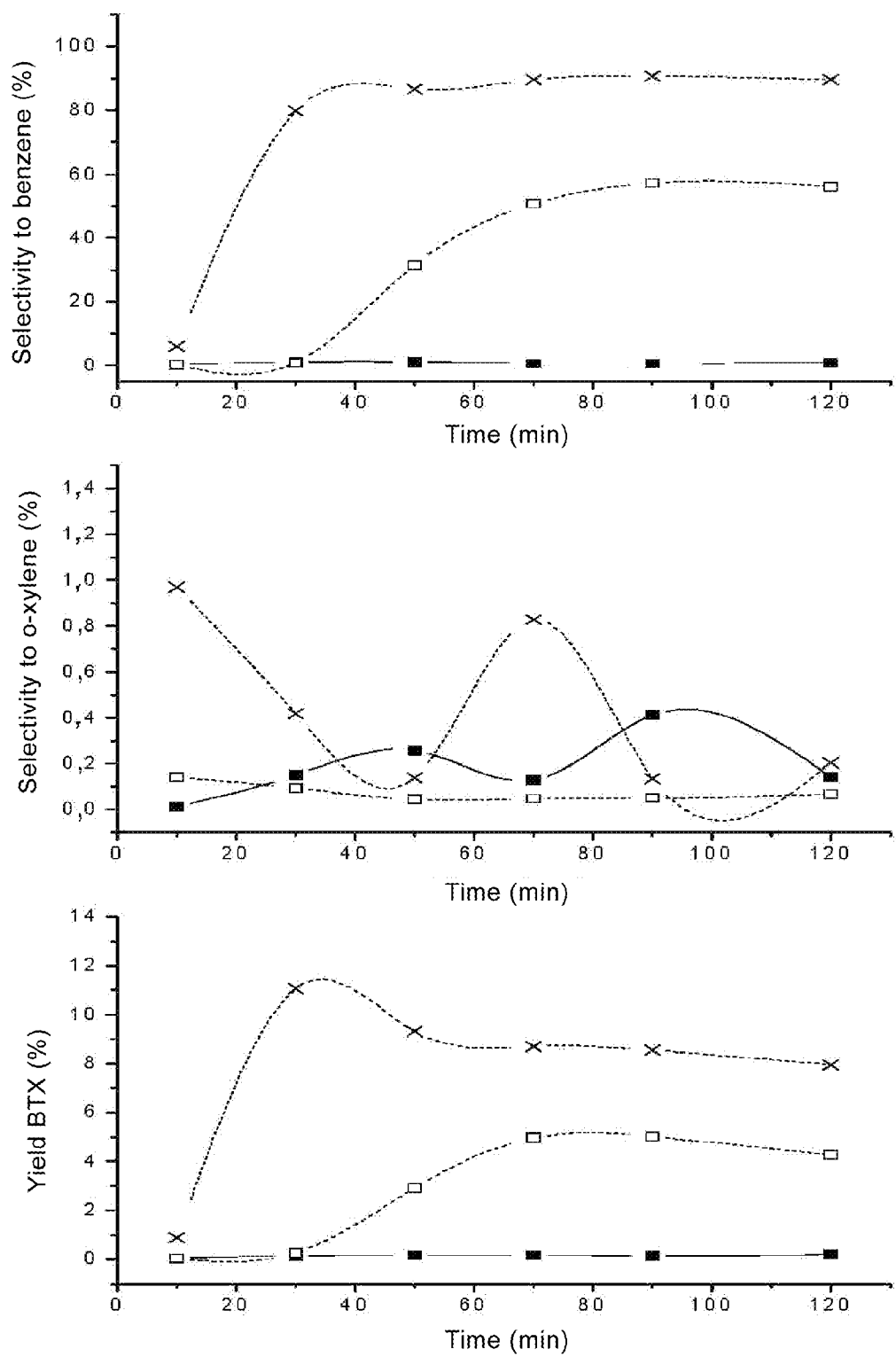
FIG. 4. Shows graphs of methane conversion and selectivity to the different reaction products and yield to BTX (benzene, toluene and xylenes) in a fluidized bed (FB) and in a two-zone fluidized bed reactor (TZFBR).
Figure 4:
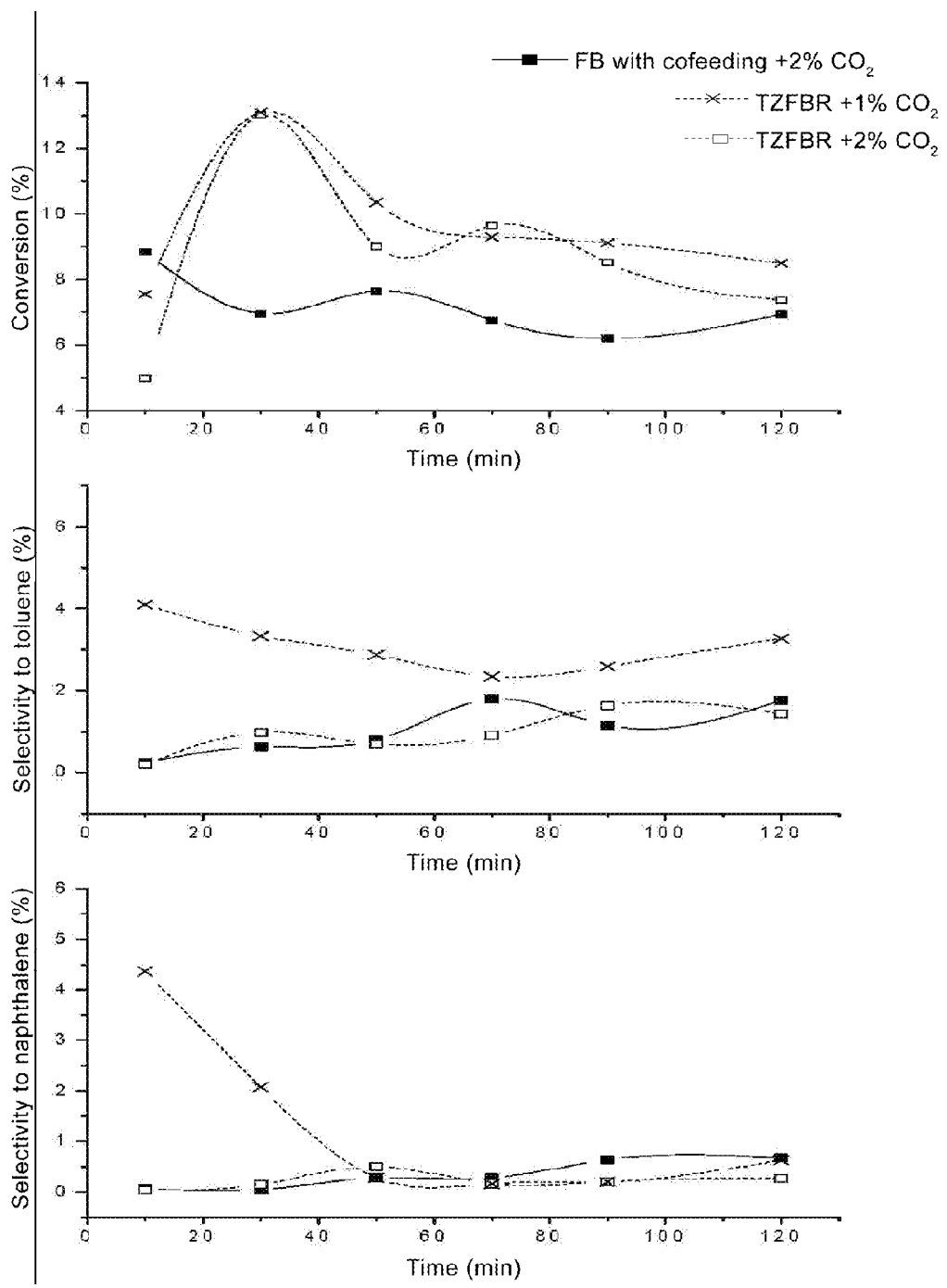
Figure 4:
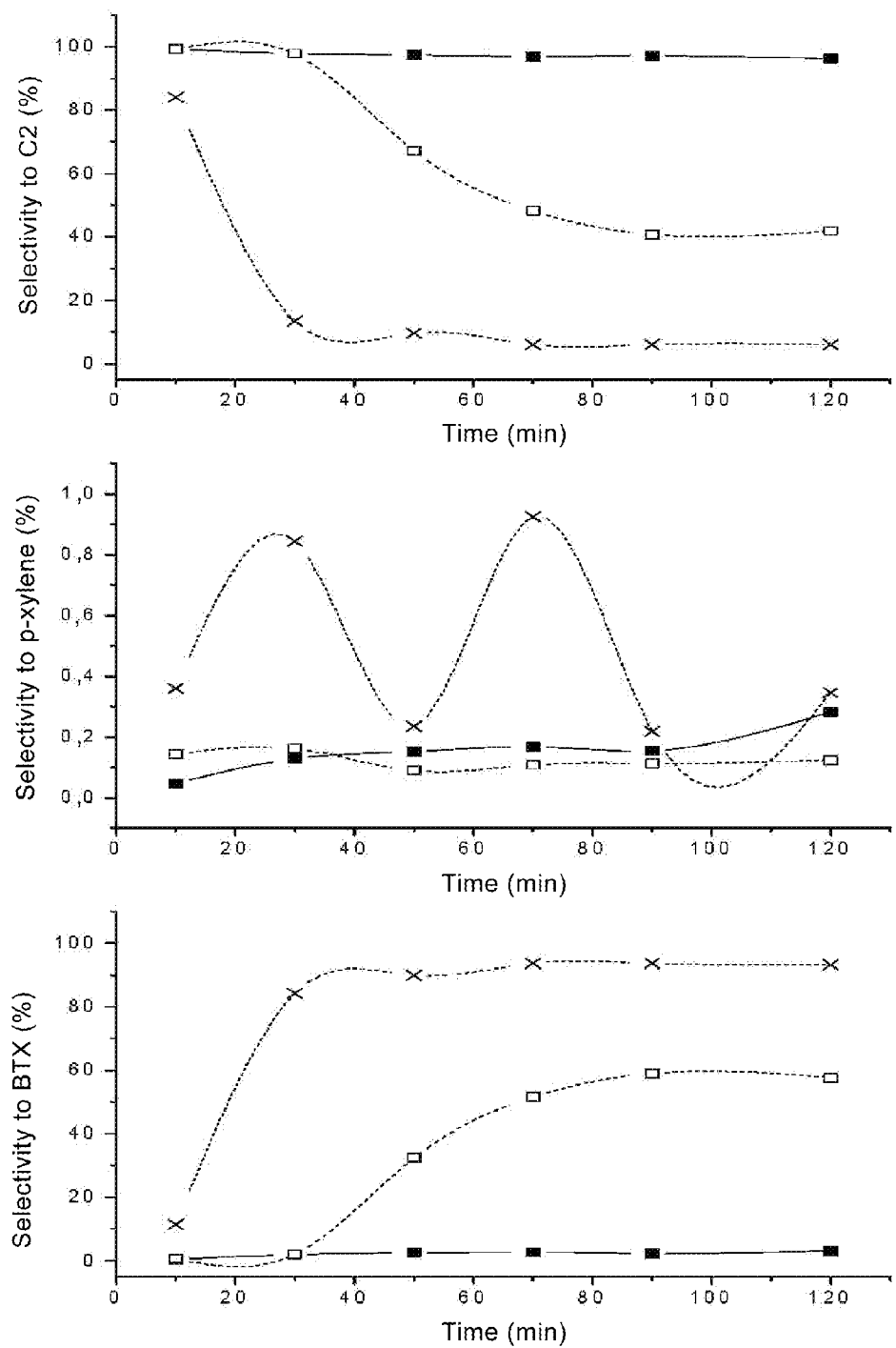

The results show how the two-zone fluidized bed reactor maintains a high selectivity to benzene and a higher and more stable methane conversion (FIG. 4) than the fixed bed reactor.

The invention claimed is:

1. A process for the aromatization of a stream containing at least one light hydrocarbon selected from among methane, ethane, ethylene, propane, propylene, butane, butene, and butadiene, which comprises: contacting the stream with a catalyst, which consists of a catalytic material and a binder, in a fluidized bed reactor,
   wherein the fluidized bed reactor has two reaction zones which consist of an oxidizing zone in a lower part of the fluidized bed and a reducing zone in an upper part of the fluidized bed, and
   wherein an oxidizing or regenerating gas is fed in the lower zone of the bed and the stream containing the light hydrocarbon is fed at an intermediate point of the bed between the oxidizing zone in the lower part of the fluidized bed and the reducing zone in the upper part of the fluidized bed.

2. The process according to claim 1, wherein the stream to be aromatized contains methane.

3. The process according to claim 1, wherein the binder is selected from among clay, silica, alumina, and aluminophosphate.

4. The process according to claim 3, wherein the binder is clay.

5. The process according to claim 1, wherein the catalytic material comprises a metal or metal compound on an inorganic support.

6. The process according to claim 5, wherein the metal is selected from among molybdenum, cobalt, rhodium, iridium, nickel, and palladium.

7. The process according to claim 6, wherein the inorganic support is a zeolite.

8. The process according to claim 1, wherein the stream further comprises at least one oxidizing or regenerating gas selected from among $H_2$, $O_2$, $CO_2$, $CO$, $H_2O$, $N_2O$, and any of their combinations, with or without inert gases.

9. The process according to claim 8, wherein the proportion of oxidizing or regenerating gases is between 1% and 20% by weight of the total stream.

10. The process according to claim 1, wherein the oxidizing or regenerating gas is selected from among $H_2$, $O_2$, $CO_2$, $H_2O$, and combinations thereof.

11. The process according to claim 10, wherein the fluidized bed reactor has greater diameter in the reducing zone than in the oxidizing zone.

12. The process according to claim 1, wherein the reducing zone comprises a membrane selective to hydrogen.

* * * * *